US007362845B2

(12) United States Patent
Ning

(10) Patent No.: US 7,362,845 B2
(45) Date of Patent: Apr. 22, 2008

(54) METHOD AND APPARATUS OF GLOBAL DE-NOISING FOR CONE BEAM AND FAN BEAM CT IMAGING

(75) Inventor: Ruola Ning, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 11/410,288

(22) Filed: Apr. 25, 2006

(65) Prior Publication Data
US 2007/0053477 A1    Mar. 8, 2007

Related U.S. Application Data

(60) Provisional application No. 60/674,335, filed on Apr. 25, 2005.

(51) Int. Cl.
*A61B 6/03*    (2006.01)
(52) U.S. Cl. .................... 378/4; 378/901; 382/131
(58) Field of Classification Search ............ 378/4, 378/901; 382/131
See application file for complete search history.

(56) References Cited

U.S. PATENT DOCUMENTS 6,480,565 B1 *  11/2002  Ning ................... 378/37

2004/0236216 A1 *  11/2004  Manjeshwar et al. ...... 600/436

OTHER PUBLICATIONS

Chen et al., Cone-beam volume CT breast imaging: wavelet analysis-based multi-resolution reconstruction and de-noising technique, Proceedings of SPIE, Medical Imaging 2002: Physics of Medical Imaging, May 2002, vol. 4682, pp. 236-244.*
Yang et al., De-noising of Cone Beam CT Image Using Wavelet Transform, 2002, SPIE vol. 4684, pp. 1077-1084.*
Ning et al., Flat Panel Detector-Based Cone-Beam Volume CT Angiography Imaging: System Evaluation, Sep. 2000, IEEE Transactions on Medical Imaging, vol. 19, No. 9, pp. 949-963.*
Kwon et al., A Generalized |w|-filter for 3-D Reconstruction, Oct. 1977, IEEE Trans. Nucl. Sci., vol. NS-24, pp. 1990-1998.*

* cited by examiner

*Primary Examiner*—Edward J. Glick
*Assistant Examiner*—John M Corbett
(74) *Attorney, Agent, or Firm*—Blank Rome LLP

(57) ABSTRACT

Raw cone beam tomography projection image data are taken from an object and are denoised by a wavelet domain denoising technique and at least one other denoising technique such as a digital reconstruction filter. The denoised projection image data are then reconstructed into the final tomography image using a cone beam reconstruction algorithm, such as Feldkamp's algorithm.

15 Claims, 2 Drawing Sheets

METHOD AND APPARATUS OF GLOBAL DE-NOISING FOR CONE BEAM AND FAN BEAM CT IMAGING

REFERENCE TO RELATED APPLICATION

The present application claims the benefit of U.S. Provisional Patent Application No. 60/674,335, filed Apr. 25, 2005, whose disclosure is hereby incorporated by reference in its entirety into the present disclosure.

STATEMENT OF GOVERNMENT INTEREST

The work leading to the present invention was supported in part by National Institutes of Health Grant No. CA094300. The government has certain rights in the invention.

FIELD OF THE INVENTION

The present invention is directed to an efficient global image denoising algorithm for cone beam and fan beam computed tomography (CT) imaging, so that the proposed algorithm can reduce the noise level while adaptively preserving the image spatial resolution, thereby reducing the radiation exposure dose for CT scanning while obtaining satisfactory image quality for diagnosis.

DESCRIPTION OF RELATED ART

It is usually considered that there are two kinds of noise in CT images. One is the continuously varying error caused by the electrical noise or roundoff errors, and the other is the discretely varying error due to the X-ray photon fluctuation. Since an important of the present invention is to account for the effect of exposure dose on image quality, that the electrical noise is assumed to be trivial enough to be negligible, and we only consider the quantum mottle, which is caused by the X-ray photon fluctuation.

FIG. 1 illustrates the projection of. an object 102 by cone type X-ray beam at an angle of $\theta$. Let the intensity of incident X-rays from the source 104 be $I_0(r,s)$, and the intensity of X-rays passed through the object 102 and incident on the flat-panel or other two-dimensional detector 106 at the location $(r,s)$ be $I_\theta(r,s)$ The projection data $P_\theta(r,s)$ can be calculated by $$P_\theta(r, s) = \ln \frac{I_0(r, s)}{I_\theta(r, s)}.$$

We can assume that the incident X-ray flux is large enough so that $I_0(r,s)$ may be considered to have negligible error. The randomness of $I_\theta(r_0,s_0)$ at location $(r_0,s_0)$ is statistically described by the Poisson probability function given by $$p\{I_\theta(r_0, s_0)\} = \frac{[\bar{I}_\theta(r_0, s_0)]^{I_\theta(r_0,s_0)}}{I_\theta(r_0, s_0)} e^{-\bar{I}_\theta(r_0,s_0)},$$

where $p\{\cdot\}$ denotes the probability and $\bar{I}_\theta(r_0,s_0)$ denotes the expected value of the measurement. Because of the randomness of $I_\theta$, the measured projection $P_\theta(r,s)$ differs from its true value. The error is caused by the noise based on the X-ray photon fluctuation. Thus, the 3-D CT image reconstructed from the projections is degraded by quantum noise from the projection $P_\theta(r,s)$.

Various denoising techniques are known in the art. Conventional denoising techniques for cone beam CT imaging or fan beam CT imaging are to directly apply denoising algorithms, such as the digital filter-based denoising technique and/or the wavelet transfer (WT)-based denoising technique, to final reconstruction images. Those methods are inefficient and time consuming DRF has the following advantages. DRF is a natural and efficient denoising tool because an appropriate reconstruction filter is mandatory for cone beam CT or fan beam CT reconstruction. Using different filters in cone beam CT reconstruction will effectively reduce the imaging noise. For example, by changing from a ramp filter to a Shepp-Logan filter, noise will be reduced by 40%. Using DRF to perform denoising is computationally efficient and will not require additional computation time. The denoise factor $(F_x)$ for DRF should be the same or close, whether it is applied to simple phantom images or to clinical images which have complicated backgrounds.

However, DRF has the following disadvantages. If only using DRF, when the required reduction factor of noise is large, significant high frequency information is also filtered out, resulting in reduced contrast (sharpness). For example, the Han-filter will reduce noise a lot (by a factor of 10) compared to the Ramp filter. However, it will also reduce high frequency information and introduce some imaging blur.

WT has the advantage of reducing noise while preserving contrast (edge sharpness). However, WT has the following disadvantages.

If $F_w$ is the reduction factor of cone beam CT image noise with a 2D (1D for fan beam CT) wavelet-transform-based denoising algorithm, if only a WT-based denoising technique is applied, then $F_w$ is not constant and uniform even for the same application. When contrast to noise ratio (CNR)$\leq$3-4, denoising is absolutely necessary to detect a low-contrast lesion with high confidence.

When a WT-based denoising technique is applied to clinical data (for example, a specimen image which represents complicated structure background), $F_w$ is also reduced significantly compared to using phantom data (simple structured background). This may be because clinical data contain much high-frequency information (edges). If all or most of the edges are kept, and background noise is selectively reduced, then the denoise factor $F_w$ will be limited because the high-frequency noise and edges are overlapped and not reduced. This becomes a disadvantage because an important real-world application of the denoising technique is for clinical data.

In addition, incorporating a WT-based technique into the reconstruction process will significantly increase computational time. For some WT-denoising techniques, it takes an average of 10-12 hours to denoise one set of projections. This will not be practical. Notice that without using WT denoising and only using the DRF denoising technique, total reconstruction time is within 5 minutes.

SUMMARY OF THE INVENTION

It is an object of the present invention to develop an efficient image denoising algorithm based on the analysis of singularity of noise wavelet transform domain It is another objection of the invention to develop such an algorithm so that the algorithm can remove the noise while adaptively preserving the image spatial resolution.

It is another object of the invention to reduce the radiation exposure dose for CT scanning while obtaining satisfactory image quality for diagnosis.

It is another object of the invention to achieve global 3D cone beam CT imaging denoising by using multi-stage and 1D or 2D Fourier transform-based and wavelet-transform-based techniques in the projection domain of cone beam CT imaging.

It is another object of the invention to maximize the noise reduction without reducing image contrast or with minimally reducing image contrast.

It is another object of the invention to maximize the potential reduction of x-ray dose without compromising image quality.

It is another object of the invention to optimize the global cone beam CT imaging denoising technique for different cone beam CT imaging applications (whole body scan, CBCT).

To achieve the above and other objects, the present invention combines wavelet transform denoising with another type of denoising such as DRF-based denoising.

After the wavelet coefficients corresponding to the noise are discarded, the inverse wavelet transform is performed to reconstruct the denoised image. After all of the filtered projection images are denoised, we can reconstruct the 3-D cone beam CT image using 3D backprojection method, for example, the Feldkamp reconstruction algorithm.

Aspects and embodiments of the invention include the following. DRF and WT-based denoising techniques can be combined and incorporated into the reconstruction process to achieve global CBCT denoising. That combination can be optimized with VOI reconstruction to measure contrast to noise ratio (CNR) and modular transfer function (MTF) using specially designed phantoms according to different applications (detector cell size (t), exposure limit and acceptable reconstruction time).

If required, additional denoising stages can be added. Such additional denoising stages include a raw projection stage ($F_{w1}$), a logarithmic and weighted projection stage ($F_{w2}$), and the use of DRF as a valve to determine how much noise and high frequency information will pass to the next denoising stage according to the requirements of the detector cell size and x-ray exposure level ($F_x$).

Artifacts and efficiency can be evaluated for clinical data. The final noise reduction factors and minimum required exposure level can be determined for the application of interest. Different CBCT denoising protocols can be incorporated with different applications and different data acquisition protocols to reduce the required x-ray dose without compromising the image quality.

The global denoising technique according to the present invention for cone beam CT imaging (fan beam CT imaging) is to apply the digital reconstruction filter (DRF)-based denoising technique and/or the wavelet transfer (WT)-based denoising technique for projection image data or filtered projection data prior to 3D backprojection process. These approaches are expected to be more effective and efficient.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
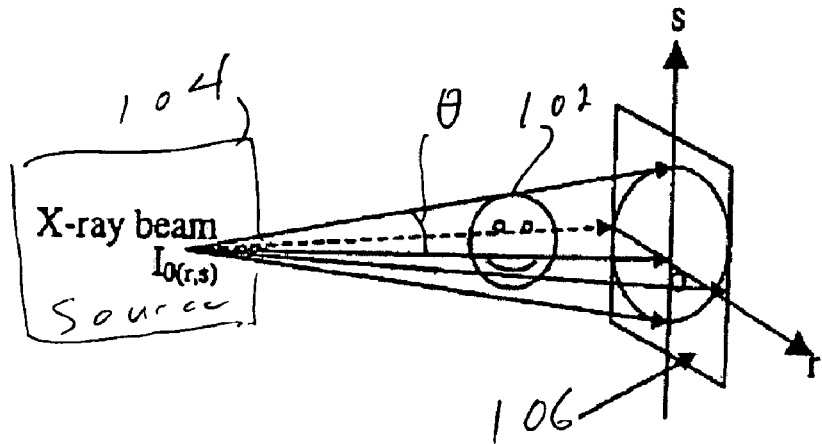
FIG. 1 shows a conventional projection imaging modality.

A preferred embodiment of the present invention will be set forth in detail with reference to the drawings, in which like reference numerals will refer to like elements or steps throughout.

Figure 2:
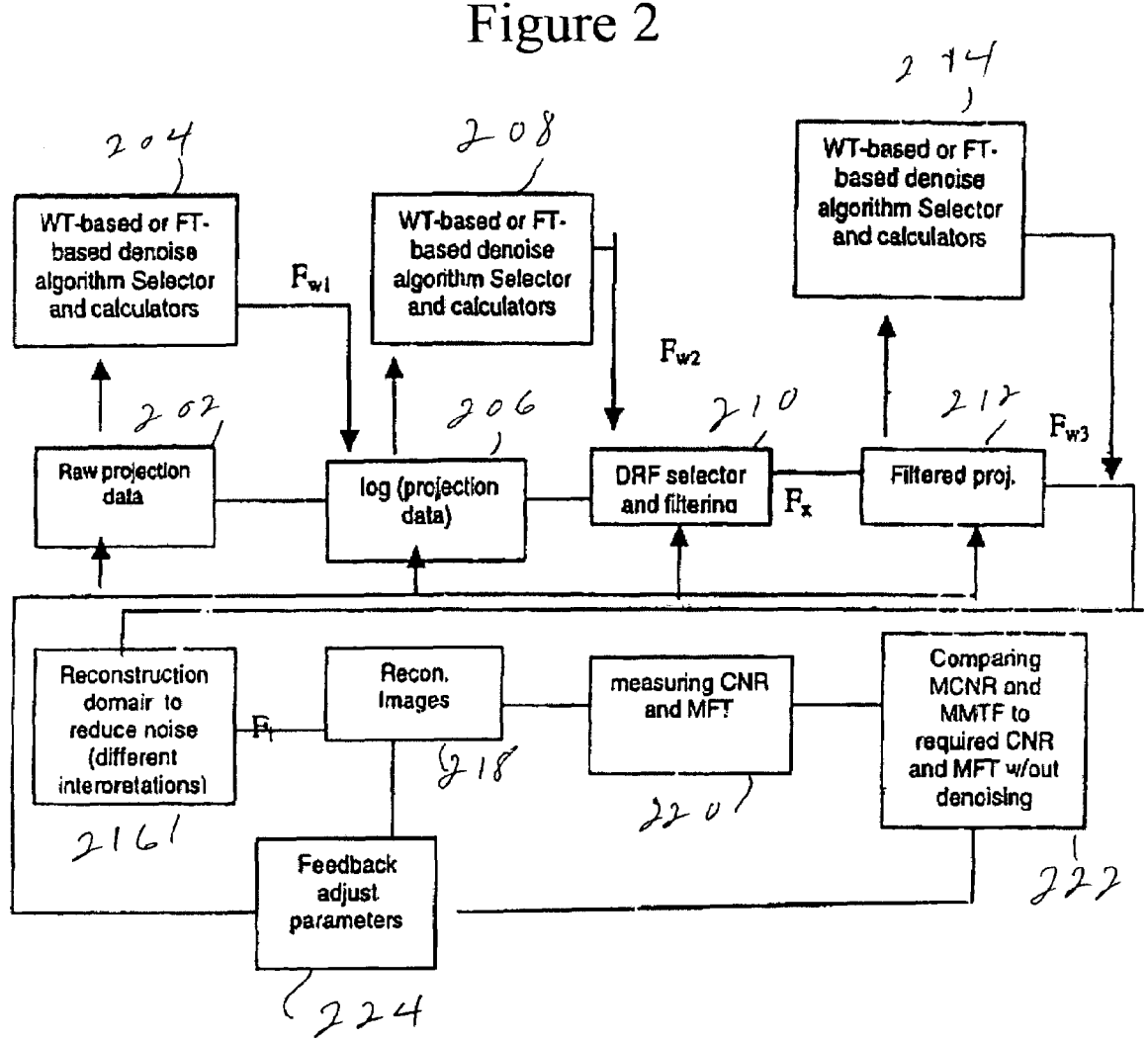
FIG. 2 shows a flow chart of the preferred embodiment.

FIG. 2 shows a flow chart of the preferred embodiment. Steps 202 through 214 are performed in the projection domain, while steps 216 through 224 are performed in the reconstruction domain.

Raw projection data taken in step 202 are applied to a WT-based or FT-based denoising algorithm selector and calculator in step 204 to produce $F_{w1}$. Also, the logarithm of the projection data is computed in step 206. $F_{w1}$ is applied to denoise the logarithm of the projection data, and the result is applied in step 208 to a WT-based or FT-based denoise algorithm selector and calculator to produce $F_{w2}$. The denoised logarithm of the projection data and $F_{w2}$ are applied to a DRF selector and filtering 210, which produces $F_x$, which is used to produce filtered projections in step 212. The filtered projections are applied in step 214 to a WT-based or FT (Fourier transform)-based denoise algorithm selector and calculator to produce $F_{w3}$.

The filtered projections and $F_{w3}$ are applied in step 216 to the reconstruction domain to reduce noise. Reconstructed images are produced in step 218 through a technique such as Feldkamp's algorithm. In step 220, CNR and MTF are measured. In step 222, those quantities are compared to the required CNR and MTF without denoising. In step 224, that comparison and the reconstructed images are used to produce feedback adjustment parameters, which are used in steps 202, 206, 210 and 212.

Figure 3:
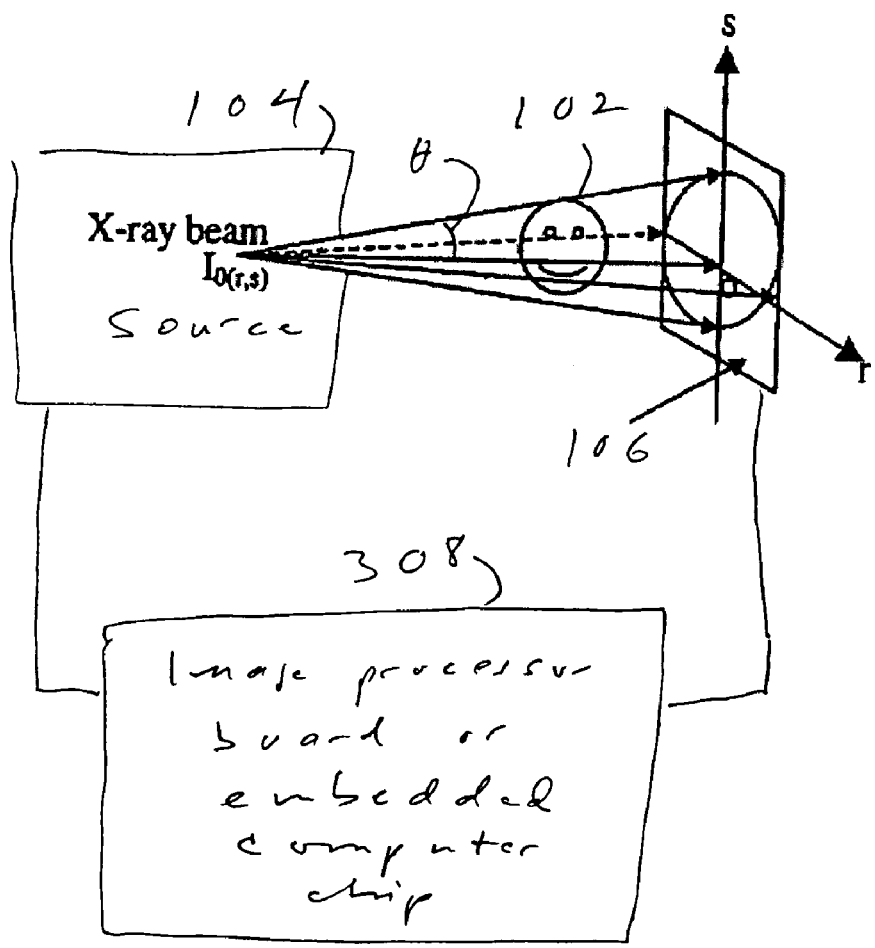
FIG. 3 shows an imaging modality in which the preferred embodiment is implemented.

Here, as shown in FIG. 3, WT-based 2D or 1 D (for fan beam case) denoising algorithms and Fourier transform-based 2D or 1D (for fan beam case) denoising algorithms can be programmed in a real time image processor board or embedded computer chip 308 to achieve fast denoising. The required denoising time for each stage should be either shorter than the total reconstruction time required without using any denoising technique or 5 minutes, whichever is shorter.

The preferred embodiment can increase the sensitivity of detecting small breast cancer without raising patient dose levels or to reduce patient dose level without compromising image quality of cone beam CT breast imaging (CBCTBI).

While a preferred embodiment of the present invention has been set forth in detail, those skilled in the art who have reviewed the present disclosure will readily appreciate that other embodiments can be realized within the scope of the present invention. For example, not all of the steps shown in FIG. 2 need to be performed in every embodiment. Moreover, other hardware implementations are possible beside that of FIG. 3. Therefore, the present invention should be construed as limited only by the appended claims.

I claim:

1. A method for producing a globally de-noised cone beam 3D image of an object, the method comprising:

(a) taking raw cone beam tomography projection image data from the object;

(b) applying a wavelet domain denoising technique to the image data;

(c) applying at least one other denoising technique to the image data, wherein said at least one other denoising technique comprises a Fourier-transform-based denoising technique;

(d) performing a reconstruction to provide feedback to the wavelet domain denoising technique and the at least one other denoising technique; and (e) reconstructing the final image from the denoised projection image data to achieve global denoising.

2. The method of claim 1, wherein said at least one other denoising technique comprises at least one other denoising technique in the projection domain.

3. The method of claim 2, wherein said at least one other denoising technique in the projection domain further comprises a digital reconstruction filter-based denoising technique.

4. The method of claim 1, further comprising applying a denoising technique in the reconstruction domain.

5. The method of claim 1, wherein step (d) comprises:
(i) measuring a quantity in the reconstructed image which represents a quality of the reconstructed image;
(ii) comparing the quantity to a required value of the quantity; and
(iii) using a result of step (d)(ii) to provide a feedback to at least one of steps (a)-(c).

6. The method of claim 5, wherein the at least one quantity comprises a contrast to noise ratio.

7. A system for producing a de-noised image of a region of interest, the system comprising:
a source of radiation providing cone beam radiation to be made incident on the region of interest;
a detector for detecting the radiation after the radiation has been made incident on the region of interest and for outputting raw cone beam tomography projection image data; and
a processing device, in electronic communication with the detector, configured to perform the steps of:
(a) taking the raw cone beam tomography projection image data from the object;
(b) applying a wavelet domain denoising technique to the image data;
(c) applying at least one other denoising technique to the image data,
wherein said at least one other denoising technique comprises a Fourier-transform-based denoising technique;
(d) performing a reconstruction to provide feedback to the wavelet domain denoising technique and the at least one other denoising technique; and
(e) reconstructing the final image from the denoised projection image data to achieve global denoising.

8. The system of claim 7, wherein said at least one other denoising technique comprises at least one other denoising technique in the projection domain.

9. The system of claim 8, wherein said at least one other denoising technique in the projection domain further comprises a digital reconstruction filter-based denoising technique.

10. The system of claim 7, wherein the processing device further applies a denoising technique in the reconstruction domain.

11. The system of claim 7, wherein the processing device performs step (d) by:
(i) measuring a quantity in the reconstructed image which represents a quality of the reconstructed image;
(ii) comparing the quantity to a required value of the quantity; and
(iii) using a result of step (d)(ii) to provide a feedback when the processing device performs at least one of steps (a)-(c).

12. The system of claim 11, wherein the at least one quantity comprises a carrier to noise ratio.

13. The system of claim 7, wherein the source comprises a source of X-rays.

14. The system of claim 7, wherein the detector comprises a two-dimensional detector.

15. The system of claim 14, wherein the two-dimensional detector is a flat-panel detector.

* * * * *